United States Patent
Jones

(10) Patent No.: US 7,147,659 B2
(45) Date of Patent: Dec. 12, 2006

(54) EXPANDABLE STENT HAVING A DISSOLVABLE PORTION

(75) Inventor: Donald K. Jones, Lauderhill, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 0 days.

(21) Appl. No.: 10/976,412

(22) Filed: Oct. 28, 2004

(65) Prior Publication Data

US 2006/0095112 A1    May 4, 2006

(51) Int. Cl.
*A61F 2/06*    (2006.01)

(52) U.S. Cl. .................. 623/1.13; 623/1.23; 623/1.35; 623/1.49

(58) Field of Classification Search ............... 623/1.13, 623/1.23, 1.35, 1.38, 1.44, 1.45, 1.46, 1.49
See application file for complete search history.

(56) References Cited

U.S. PATENT DOCUMENTS

| | | | |
|---|---|---|---|
| 4,743,252 A | 5/1988 | Martin, Jr. et al. | |
| 5,064,435 A | 11/1991 | Porter | |
| 5,100,429 A | 3/1992 | Sinofsky et al. | |
| 5,609,628 A | 3/1997 | Keranen | |
| 5,617,878 A * | 4/1997 | Taheri | 128/898 |
| 5,665,063 A | 9/1997 | Roth et al. | |
| 5,702,418 A | 12/1997 | Ravenscroft | |
| 5,713,917 A | 2/1998 | Leonhardt et al. | |
| 5,749,919 A | 5/1998 | Blanc | |
| 5,755,773 A | 5/1998 | Evans et al. | |
| 5,769,884 A | 6/1998 | Solovay | |
| 5,921,954 A | 7/1999 | Mohr, Jr. et al. | |
| 5,951,599 A | 9/1999 | McCrory | |
| 6,004,261 A | 12/1999 | Sinofsky et al. | |
| 6,030,414 A | 2/2000 | Taheri | |
| 6,102,938 A | 8/2000 | Evans et al. | |
| 6,254,628 B1 | 7/2001 | Wallace et al. | |
| 6,290,673 B1 | 9/2001 | Shanley | |
| 6,395,018 B1 | 5/2002 | Castaneda | |
| 6,497,722 B1 | 12/2002 | Von Oepen et al. | |
| 6,524,335 B1 | 2/2003 | Hartley et al. | |
| 6,533,811 B1 * | 3/2003 | Ryan et al. | 623/1.23 |
| 6,569,195 B1 | 5/2003 | Yang et al. | |
| 6,605,111 B1 | 8/2003 | Bose et al. | |
| 6,673,106 B1 | 1/2004 | Mitelberg et al. | |
| 6,712,845 B1 * | 3/2004 | Hossainy | 623/1.42 |
| 6,723,116 B1 * | 4/2004 | Taheri | 623/1.11 |
| 6,790,224 B1 * | 9/2004 | Gerberding | 623/1.12 |
| 6,833,003 B1 | 12/2004 | Jones et al. | |
| 2001/0037145 A1 | 11/2001 | Guruwalya et al. | |
| 2002/0035394 A1 | 3/2002 | Fierens et al. | |
| 2002/0072790 A1 | 6/2002 | McGuckin, Jr. et al. | |
| 2002/0072792 A1 | 6/2002 | Burgermeister et al. | |

(Continued)

OTHER PUBLICATIONS

U.S. Appl. No. 10/696,667, filed Oct. 29, 2003, Pomeranz et al.

(Continued)

*Primary Examiner*—Corrine McDermott
*Assistant Examiner*—Thomas Sweet
(74) *Attorney, Agent, or Firm*—Henry W. Collins

(57) ABSTRACT

An expandable stent having a covering which exhibits the characteristic of upon being activated by applying an agent to the covering, dissolving to expose a portion of the underlying stent. The stent may be placed across the neck of an aneurysm to seal the aneurysm and thereafter a selected region of the covering may be dissolved by an activating agent to permit blood to flow to adjacent vessels.

4 Claims, 3 Drawing Sheets

U.S. PATENT DOCUMENTS

| | | |
|---|---|---|
| 2002/0123788 A1* | 9/2002 | Sanders Millare et al. ... 623/1.13 |
| 2002/0123801 A1 | 9/2002 | Pacetti et al. |
| 2002/0128706 A1 | 9/2002 | Osypka |
| 2002/0193872 A1 | 12/2002 | Trout, III et al. |
| 2002/0193873 A1 | 12/2002 | Brucker et al. |
| 2003/0074049 A1 | 4/2003 | Hoganson et al. |
| 2003/0109917 A1 | 6/2003 | Rudin et al. |
| 2003/0135265 A1 | 7/2003 | Stinson |
| 2003/0139802 A1 | 7/2003 | Wulfman et al. |
| 2003/0153972 A1 | 8/2003 | Helmus |
| 2003/0208256 A1 | 11/2003 | DiMatteo et al. |
| 2004/0006381 A1 | 1/2004 | Sequin et al. |
| 2004/0030380 A1 | 2/2004 | Shulze et al. |
| 2004/0044396 A1 | 3/2004 | Clerc et al. |
| 2004/0098117 A1 | 5/2004 | Hosainy et al. |
| 2004/0106972 A1* | 6/2004 | Deaton ... 623/1.1 |

OTHER PUBLICATIONS

U.S. Appl. No. 10/975,842, filed Oct. 28, 2004, Jones et al.

* cited by examiner

EXPANDABLE STENT HAVING A DISSOLVABLE PORTION

BACKGROUND OF INVENTION

1. Field of the Invention

The present invention relates to intravascular stents and methods of treating aneurysms, and more particularly, this invention relates to a covered stent which may be modified to treat an aneurysm located adjacent to a bifurcated blood vessel while permitting blood to flow through the bifurcated vessel, and methods of use thereof.

2. Description of the Prior Art

Expandable stents are widely used in the treatment of vascular diseases. Typically, a stent is inserted into a stenosed blood vessel after an angioplasty to prevent the restenosis of the blood vessels. Expandable stents are also used as aneurysm covers. When a stent is placed across an aneurysm, the blood flow into the aneurysm is decreased. Decreased blood flow within an aneurysm promotes the formation of a thrombus within the aneurysm which ultimately aids in protecting the aneurysm from further expansion or rupture.

Optimally, a covered stent is positioned across an aneurysm to completely restrict the blood flow into the aneurysm. Such covered stents, typically covered with a material such as PTFE provide suitable aneurysm covers; however, these stents have certain limitations. For example, covered stents impede blood flow into or out of branching blood vessels. Thus, a covered stent may not be suitable for treating an aneurysm at or near a bifurcated blood vessel.

Several patents and patent applications disclose covered stents with various modifications which tend to avoid these limitations inherent with typical covered stents. For example, U.S. Pat. No. 6,030,414, entitled "Variable Stent And Method For Treatment Of Arterial Disease," discloses a covered stent having predetermined and sized lateral openings for the treatment of arterial disease at or around the intersection of multiple arteries; U.S. Pat. No. 6,497,722, entitled "Method And Apparatus For In-Vivo Tailored Stents Indicated For Use In Tortuous Anatomy," discloses a stent having a side opening to allow unimpeded blood flow to a branching vessel at the point of stenting; and, U.S. Patent Application Publication No. 2003/0074049, entitled "Covered Stents And Systems For Deploying Covered Stents," discloses a covered stent which may be perforated in order to allow blood flow into a side branch or bifurcated vessel.

Also, U.S. patent application Ser. No. 10/696,667, filed on Oct. 29, 2003, assigned to the same assignee as the subject patent application discloses a covered stent for treating an aneurysm which includes a skeletal stent structure with removable slat members to permit blood to flow through a bifurcated blood vessel. Upon deployment, one or more of the slats may be removed to allow blood to flow through portions of the stent structure while others of the slats are left in place to seal the neck of an adjacent aneurysm. This patent application made of record in the subject patent application and is hereby incorporated and made a part of the subject application.

SUMMARY OF THE INVENTION

In accordance with one aspect of the present invention there is provided an aneurysm treatment device including an expandable stent which takes the form of a small diameter skeletal tubular member having a thin wall. The wall of the skeletal tubular member defines a plurality of cells which are formed by a plurality of interconnected strut members. Also, a covering extends over a portion of the expandable stent. The covering exhibits the characteristic of, upon being actuated by applying an activating agent to the covering, dissolving to thereby expose a portion of the expandable stent.

In accordance with another aspect of the present invention, the expandable stent takes the form of a metallic structural tubular member and the covering is formed from a polymer, such as ethylene vinyl alcohol. The activating agent may take the form of dimethylsulfoxide. If the activating agent is applied to a selective portion of the coating that portion dissolves to expose the underlying porous stent to permit blood to flow through the stent while the balance of the stent remains intact to cover an aneurysm.

In accordance with another aspect of the present invention, there is provided a method of treating an aneurysm including the method steps of providing an expandable stent including a skeletal tubular member having a covering disposed onto the skeletal tubular member, inserting the expandable stent into the blood vessel of a patient, advancing the expandable stent until the covering on the stent is aligned with and covers an aneurysm in the blood vessel, expanding the expandable stent so that the covering extends across the neck of an aneurysm, and applying an activating agent to a portion of the covering to cause that portion of the covering to dissolve to expose a portion of the underlying stent in order to permit blood to flow through that portion of the stent while maintaining a seal across the aneurysm.

In accordance with another aspect of the present invention there is provided a method for treating an aneurysm including the steps of providing an expandable stent including a skeletal tubular member having a covering disposed onto the skeletal tubular member, inserting said expandable stent into a blood vessel of a patient, advancing the expandable stent until the covering on the stent is aligned with and covers an aneurysm in the blood vessel and also covers a branching blood vessel, expanding the skeletal tubular member so that the covering extends across the neck of the aneurysm and across a branching vessel, inserting a drug delivery catheter into the branching vessel and advancing the distal tip of the drug delivery catheter to have position proximate to a portion of the covering of the stent which extends across the branching vessel, and applying an activating agent through the drug delivery catheter to that portion of the covering to thereby cause that portion of the covering to dissolve and expose a portion of the porous tubular member thereby permitting blood to flow to or from the branching vessel.

In accordance with still another aspect of the present invention, there is provided an aneurysm treatment device which includes an expandable tubular member having a thin wall and in which the wall of the tubular member is formed of a material which exhibits the characteristic that when an activating agent is applied to a portion of the wall of the tubular member that portion of the wall dissolves to provide a passageway through the wall. The wall of the expandable tubular member may be formed of ethylene vinyl alcohol and the activating agent may take the form of dimethylsulfoxide.

DESCRIPTION OF THE PREFERRED EMBODIMENT

Figure 1:
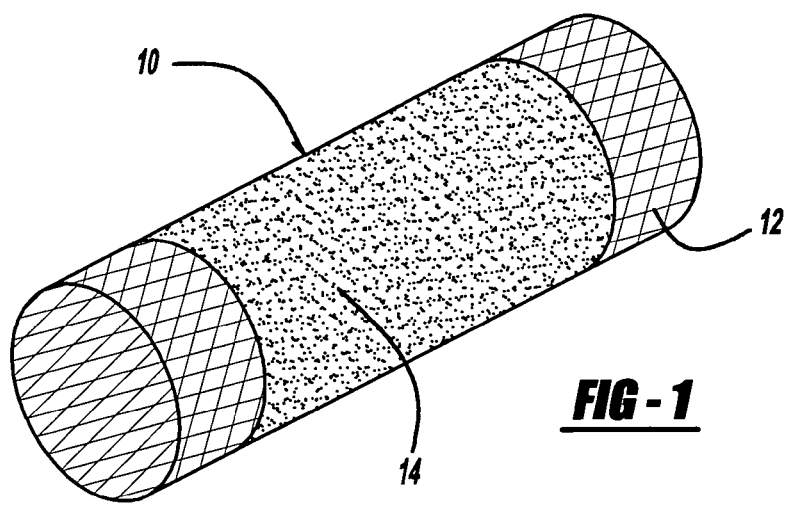
FIG. 1 is an enlarged oblique view of a covered stent device comprised of an expandable skeletal support member and a outer covering which extends over a portion of the support member.

FIG. 1 illustrates an expandable covered stent 10 which may be used to treat an aneurysm, such as an aneurysm within the brain, occurring in a blood vessel at or near a bifurcation in the blood vessel. In the preferred embodiment of the present invention, the covered stent 10 is comprised of an expandable skeletal stent 12 and an outer covering 14 disposed on the outer surface of the skeletal stent 12.

More particularly, the skeletal stent 12 includes a plurality of cells which are formed by a plurality of interconnected strut members to thereby define a structure which may be placed into a vessel and after being properly aligned may then be expanded. The skeletal stent 12 may either take the form of a balloon expandable stent or a self expanding stent. An example of such a self expanding stent is disclosed in U.S. Pat. No. 6,673,106, entitled, "Intravascular Stent Device," and an example of a stent and stent deployment system is disclosed in U.S. patent application Ser. No. 10/365,288, entitled, "Expandable Stent And Delivery System," filed on Feb. 12, 2003. This patent and patent application are assigned to the same assignee as the present patent application and are hereby made of record and incorporated by reference into the present patent application.

The outer covering 14 preferably takes the form of a polymer, such as a thin film of ethylene vinyl alcohol which may be bonded to the surface of the skeletal stent 12. This covering, as will be described in more detail, serves to cover the neck of the aneurysm. This material exhibits the characteristic of, upon being activated by applying an agent to the covering, dissolving to expose a portion of the underlying expandable stent.

Figure 2:
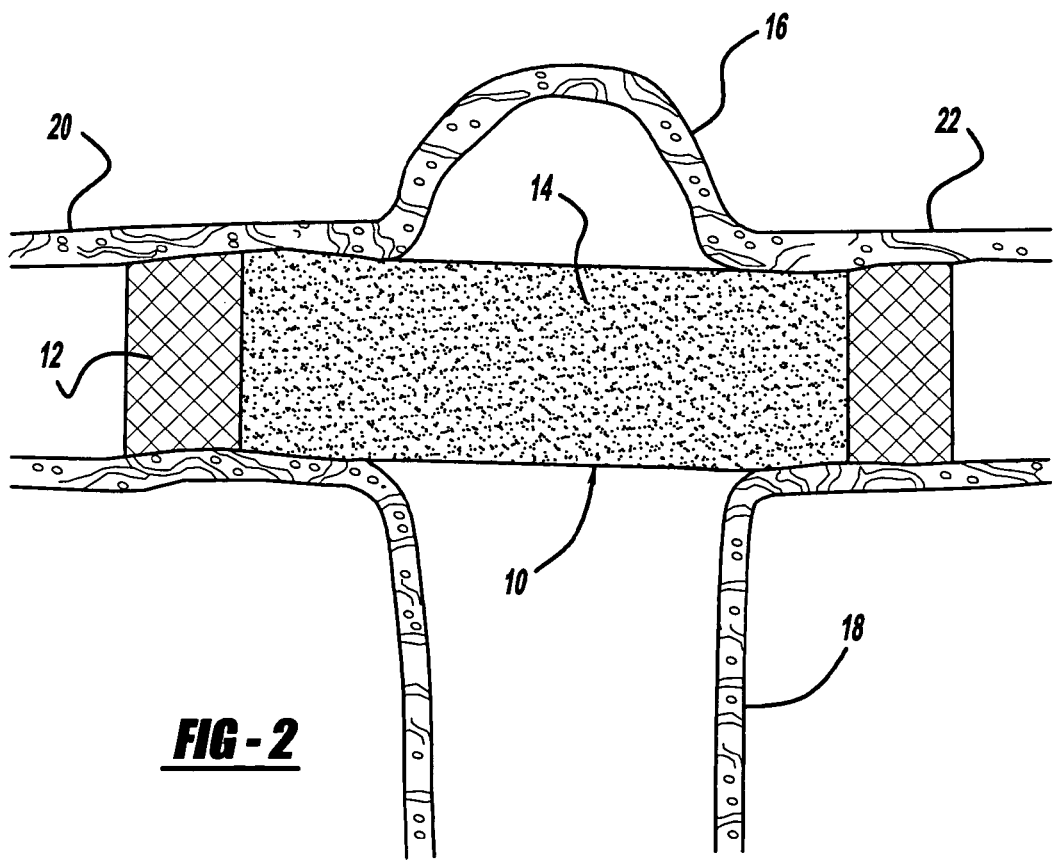
FIG. 2 is an enlarged elevational view of the covered stent placed adjacent to the neck of an aneurysm and across a main artery at a bifurcation.

FIG. 2 illustrates the covered stent 10 of FIG. 1 positioned within a blood vessel such that the outer covering 14 extends across the neck of an aneurysm 16. As with almost all vascular stents, the covered stent is initially compressed and is passed through the vessel and is then expanded with a balloon catheter or is permitted to self expand into the position as shown. Also, since the aneurysm 16 occurs at a location adjacent to a parent vessel 18 which serves to feed the branch vessels 20, 22, with the placement of the stent with the outer covering 14 covering the neck of the aneurysm 16, it will also obstruct the flow of blood from the parent vessel 18 into the branching vessels 20, 22. Aneurysms frequently occur at a bifurcated junction vessels, therefore, it should be observed that one of the major advantages of the present invention is that of providing a covered stent which serves to provide a covering for the neck of the aneurysm while at the same time being modified to allow blood to flow from a bifurcated vessel to other vessels. This modification will be explained in more detail with respect to the following drawings.

Figure 3:
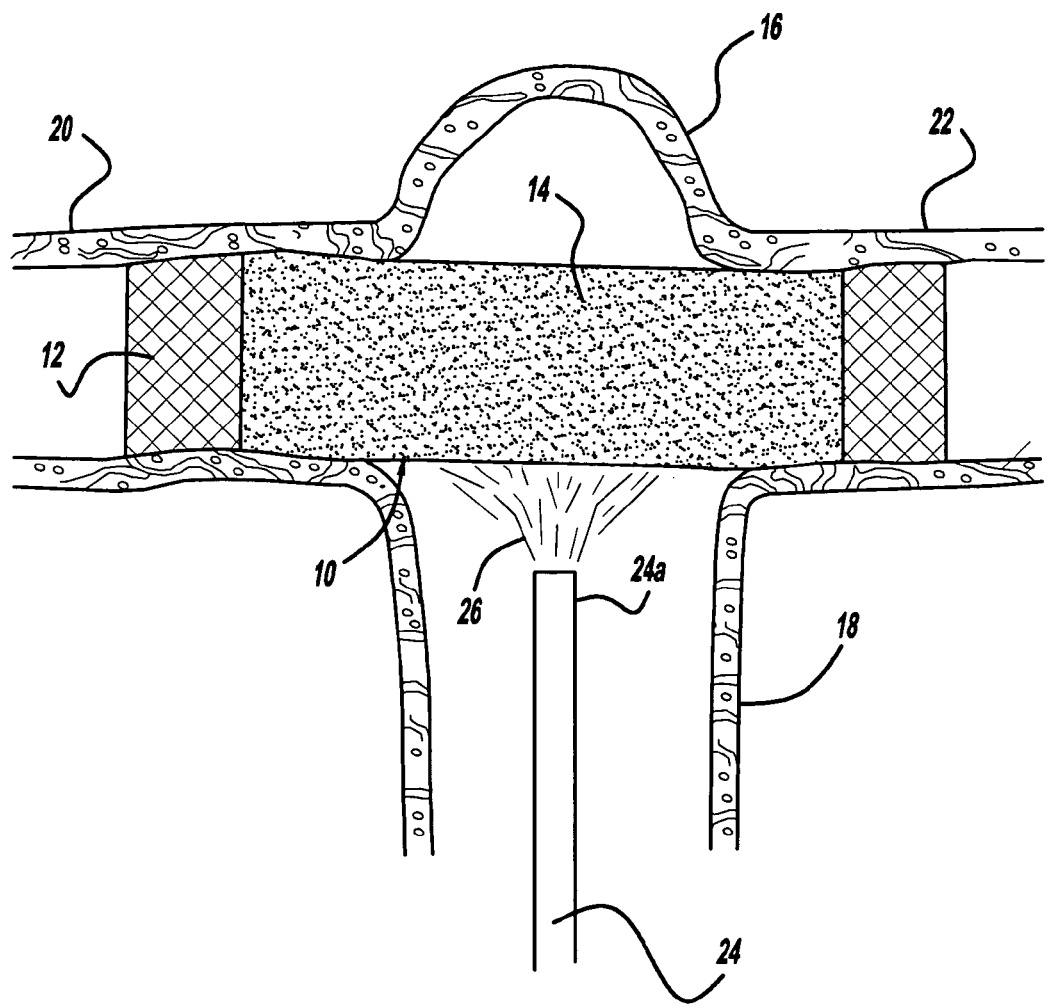
FIG. 3 is an enlarged elevational view of the covered stent illustrating an activating agent being applied to a portion of the covering device at a branching vessel; and, FIG. 4 is an enlarged elevational view of the covered stent with a portion of the covering removed to expose the underlying porous skeletal stent.

FIG. 3, which is similar to FIG. 2, illustrates the covered stent 10 which extends from the branch vessel 20 to the branch vessel 22 and is positioned so that the outer covering 14 occludes both the aneurysm 16 and the parent vessel 18.

Once the covered stent 10 is properly placed within the blood vessels, a drug delivery catheter 24 may be inserted into the vasculature and passed through the parent vessel 18 so that the distal end 24a of the drug delivery catheter is positioned in proximity to the outer covering 14 of the covered stent 10 at a region 24a where the outer covering 14 occluded the parent vessel 18. With the outer covering 14 formed of a thin film of ethylene vinyl alcohol, preferably an activating agent 26 such as, for example, dimethylsulfoxide, is applied to the outer covering 14 in the region where the outer covering 14 occludes the parent vessel 18.

Figure 4:
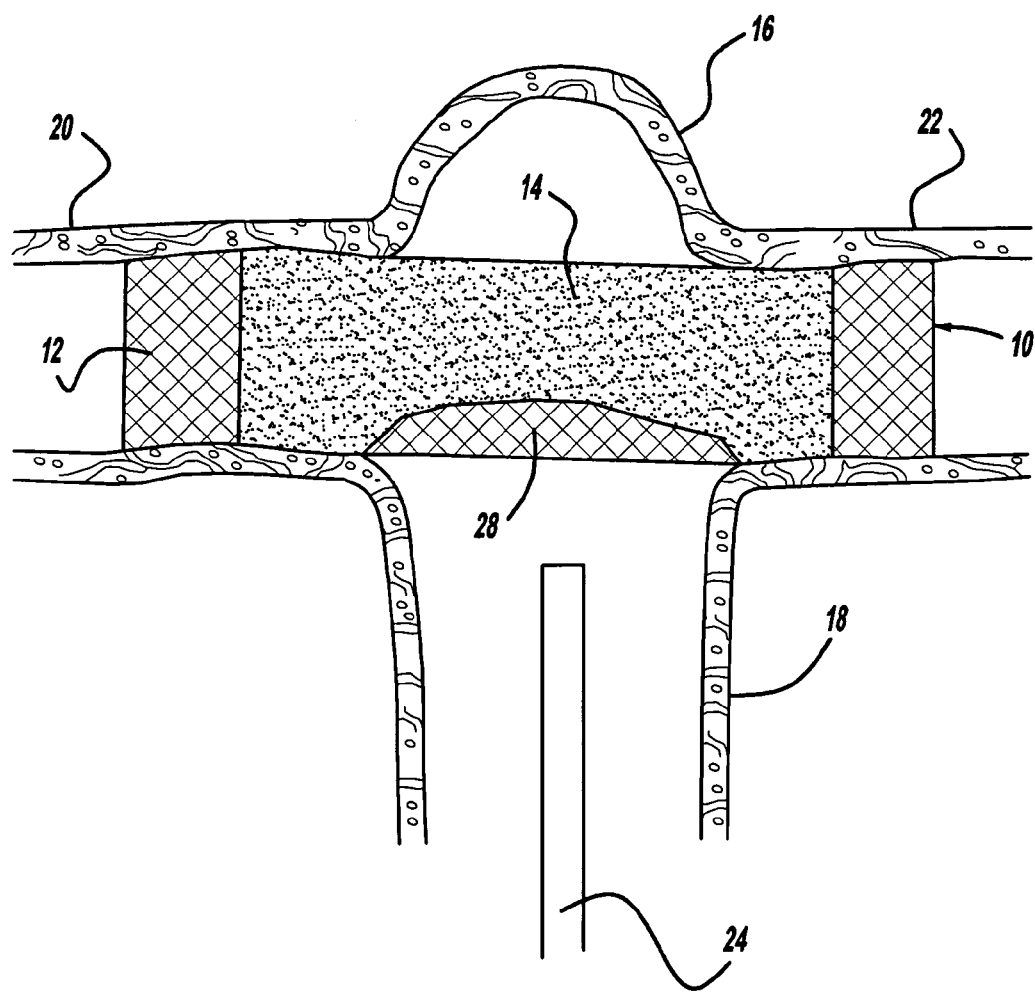

FIG. 4 illustrates the covered stent 10 after application of the activating agent and, as is apparent, the activating agent, or dimethylsulfoxide, has dissolved the covering formed of ethylene vinyl alcohol in the desired region of the parent vessel 18 to thereby expose the underlying porous skeletal stent 12 at location 28. The drug delivery catheter 24 is then removed from the vasculature, with the result that the covered stent 10 serves to occlude the neck of the aneurysm 16 while permitting blood to flow through the parent vessel 18 and into the branch vessels 20, 22.

In summary, the device of the present invention may be used to treat an aneurysm by providing an expandable stent including a skeletal tubular member having a covering disposed onto the skeletal member, inserting the expandable stent into a blood vessel of a patient, advancing the expandable stent until the covered stent is aligned with and covers an aneurysm in the blood vessel, expanding the skeletal tubular member so that the covering extends across the neck of the aneurysm, and applying an activating agent to a portion of the covering to cause that portion of the covering to dissolve and expose a portion of the underlying skeletal tubular member. Once this method has been performed, the remaining portion of the covering serves as a seal for the aneurysm while permitting blood to flow through all of the adjacent vessels.

A novel medical device and method to treat an aneurysm at a bifurcation has been disclosed. Although a preferred embodiment of the present invention has been described, it should be understood that various modifications such as for example removal of a portion of the covering by an electrical or electrolytic process, by a heating process or by other processes may be made by one skilled in the art without departing from the scope of the claims which follow.

What is claimed is:

1. A method of treating an aneurysm comprising:
providing an expandable covered stent including a skeletal tubular member having a covering disposed onto the skeletal tubular member;
inserting said covered stent into a blood vessel of a patient;
advancing said covered stent until the covering of the stent is aligned with and is adjacent to a neck of an aneurysm in the blood vessel;
expanding said skeletal tubular member so that said covering extends across the neck of the aneurysm; and,
applying an activating agent to a skeletal portion of said covering to cause that portion of said covering to dissolve and expose a portion of the skeletal tubular member in order to permit blood to flow through adjacent blood vessels.

2. A method of treating an aneurysm as defined in claim 1, wherein the covering is ethylene vinyl alcohol and the activating agent is dimethylsulfoxide.

3. A method of treating an aneurysm comprising:

providing an expandable covered stent including a skeletal tubular member having a covering disposed onto the skeletal tubular member;

inserting said covered stent into a blood vessel of a patient;

advancing said covered stent until the covering of the stent is aligned with and is adjacent to a neck of an aneurysm in the blood vessel and also covers a branching blood vessel;

expanding said skeletal tubular member so that said covering extends across the neck of the aneurysm;

inserting a drug delivery catheter into a branching vessel of the patient and advancing a distal tip of the drug delivery catheter to a position proximate to a portion of said covering of the covered stent; and, applying an activating agent through said drug delivery catheter to said portion of said covering to cause that portion of said covering to dissolve and expose a desired region of the skeletal tubular member in order to permit blood to flow through a parent vessel and adjacent vessels.

4. A method of treating an aneurysm as defined in claim 3, wherein the covering is ethylene vinyl alcohol and the activating agent is dimethylsulfoxide.

* * * * *